United States Patent
Yamamoto et al.

(10) Patent No.: US 7,879,586 B2
(45) Date of Patent: Feb. 1, 2011

(54) GENE ENCODING METHYLATED CATECHIN SYNTHASE

(75) Inventors: Mari Yamamoto, Shizuoka (JP); Masanobu Kirita, Ibaraki (JP); Manabu Sami, Ibaraki (JP); Mitsuo Ikeda, Ibaraki (JP)

(73) Assignees: Incorporated Administrative Agency National Agriculture and Food Research Organization, Ibaraki (JP); Asahi Breweries, Ltd., Tokyo (JP)

( * ) Notice: Subject to any disclaimer, the term of this patent is extended or adjusted under 35 U.S.C. 154(b) by 699 days.

(21) Appl. No.: 11/667,590

(22) PCT Filed: Nov. 14, 2005

(86) PCT No.: PCT/JP2005/020793

§ 371 (c)(1),
(2), (4) Date: Oct. 25, 2007

(87) PCT Pub. No.: WO2006/054500

PCT Pub. Date: May 26, 2006

(65) Prior Publication Data

US 2008/0318272 A1  Dec. 25, 2008

(30) Foreign Application Priority Data

Nov. 17, 2004 (JP) ............................. 2004-333290

(51) Int. Cl.
| | |
|---|---|
| C12P 21/00 | (2006.01) |
| C12N 15/00 | (2006.01) |
| C12N 1/21 | (2006.01) |
| C12N 5/10 | (2006.01) |
| C12N 5/04 | (2006.01) |
| C12Q 1/48 | (2006.01) |
| C07H 21/00 | (2006.01) |
| C12N 9/10 | (2006.01) |
| C07K 14/00 | (2006.01) |

(52) U.S. Cl. ............... 435/193; 435/320.1; 435/252.3; 435/325; 435/410; 435/69.1; 435/15; 536/23.2; 530/350

(58) Field of Classification Search ............... 435/193, 435/69.1, 320.1, 252.3, 325, 15, 3; 530/350; 536/23.2
See application file for complete search history.

(56) References Cited

U.S. PATENT DOCUMENTS 6,465,229 B2 * 10/2002 Cahoon et al. ............... 435/193

OTHER PUBLICATIONS

Tang et al., GenBank accession No. AAT37172, May 2004.*
Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Kappel et al., Current Opinion in Biotechnology 3:548-553, 1992.*
Mullins et al., Hypertension 22(4):630-633, 1993.*
Cameron, E., Molecular Biotechnology 7:253-265, 1997.*
Houdebine, L., Journal of Biotechnology 98:145-160, 2002.*
Phillips, A., J. Pharm. Pharmacology 53:1169-1174, 2001.*
Gardlik et al., Med. Sci. Monit. 11(4):RA110-121, 2005.*
Tang et al., GenBank accession No. AY600140, May 2004.*
G. Busam et al., "Characterization and Expression of Caffeoyl-Coenzyme A 3-O-Methyltransferase Proposed for the Induced Resistance Response of *Vitis vinifera* L.", Plant Physiol., vol. 115, pp. 1039-1048, 1997.
Meyerrnans H et al. Modifications in Lignin and Accumulation of Phenolic Glucosides in Poplar Xylem upon Down-regulation of Caffeoyl-Coenzyme A O-Methyltransferase, an Enzyme Involved in Lignin Biosynthesis J. Biol. Chem. 2000 275: 36899-36909. First Published, JBC Papers in Press, Aug. 8, 2000 (cited in European Search Report for corresponding application EP 05806065).
Database Uniprot [Online], Jul. 5, 2004, Database Accession No. Q6PUA7 (cited in European Search Report for corresponding application EP 05806065).

* cited by examiner

*Primary Examiner*—Delia M Ramirez
(74) *Attorney, Agent, or Firm*—Wenderoth, Lind & Ponack, L.L.P.

(57) ABSTRACT

A gene encoding a methylated catechin synthase that can effectively synthesize methylated catechins having high antiallergic activity.

The gene encoding a methylated catechin synthase contains at least one nucleotide sequence selected from the group consisting of SEQ ID NOs: 1, 3 and 5.

7 Claims, 1 Drawing Sheet

GENE ENCODING METHYLATED CATECHIN SYNTHASE

This application is a U.S. national stage of International Application No. PCT/JP2005/020793 filed Nov. 14, 2005.

TECHNICAL FIELD

The present invention relates to a gene encoding methylated catechin synthase, an enzyme that synthesizes methylated catechin using as a substrate epigallocatechin-3-O-gallate, epicatechin-3-O-gallate or an isomer thereof. The present invention also relates to a plasmid that incorporates the methylated catechin synthase gene, a transformed organism with the plasmid, a method for producing methylated catechin synthase using the transformed organism, and a method for producing methylated catechin using the methylated catechin synthase obtained by the production method.

BACKGROUND ART

Epigallocatechin-3-O-gallate derivatives represented by the following general formula (I):

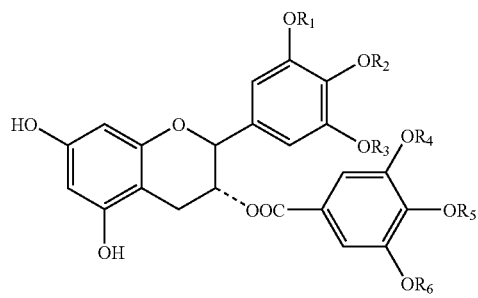

(I)

[wherein $R_1$ through $R_6$ are each a hydrogen atom or a methyl group and at least one of $R_1$ through $R_6$ is a methyl group], epicatechin-3-O-gallate derivatives represented by the following general formula (II):

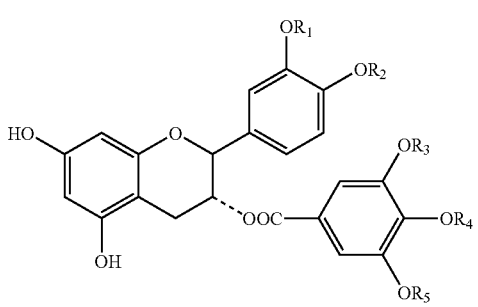

(II)

[wherein $R_1$ through $R_5$ are as defined above and at least one of $R_1$ through $R_5$ is a methyl group] and isomers thereof are naturally occurring compounds that serve as effective antiallergic agents. These compounds are obtained by methylation of epigallocatechin-3-O-gallate represented by the following chemical formula (III):

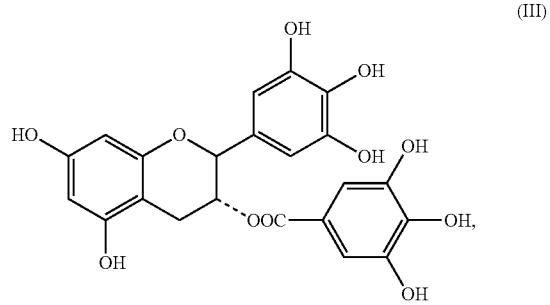

(III)

epicatechin-3-O-gallate represented by the following chemical formula (IV):

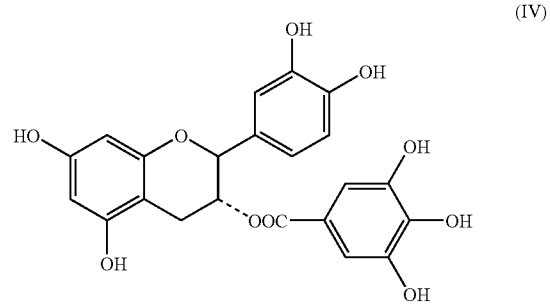

(IV)

or isomers thereof (Patent Document 1 and Non-Patent Document 1).

The number of allergy patients is rapidly increasing due to changes in the living environment in recent years. The treatment of allergic diseases generally takes a long time and patients are strongly recommended to eat food products that do not cause side effects and can be safely eaten everyday in order to alleviate these diseases. Thus, there is a great need for such food products. Epigallocatechin-3-O-gallate (which may be referred to simply as "EGCG," hereinafter) is a major component present in tea that is known to have antiallergic activity (Non-Patent Document 2). The compound has a structure represented by the following chemical formula (V):

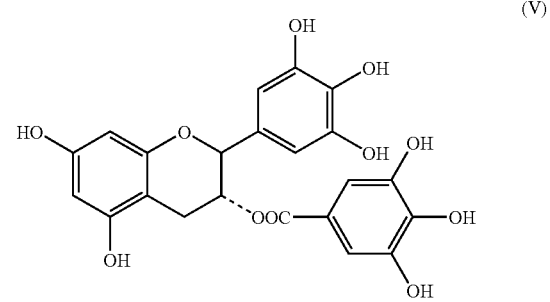

(V)

Recent studies have revealed that epigallocatechin-3-O-(3-O-methyl)gallate, epicatechin-3-O-(3-O-methyl)gallate and the like have even higher antiallergic activity (Patent Document 1, Non-Patent Document 1).

Yabukita, one of the most common cultivars of tea, is known to contain significant amounts of EGCG but no methylated catechins such as epigallocatechin-3-O-(3-O-methyl) gallate and epicatechin-3-O-(3-O-methyl)gallate. While some tea cultivars, including Seishin dai-pan, Benihomare, Benifuji and Benifuki, contain abundant methylated catechins, most of them are rare and difficult to obtain. Thus, a way is needed to convert readily available EGCG into more valuable methylated catechins.

Although several processes for methylating EGCG have been proposed in Non-Patent Document 3, Patent Document 2 and Patent Document 3, each relies upon chemical synthesis or modification and can hardly be used to specifically methylate the hydroxyl groups at positions 3, 4 and 5 of the galloyl group, as represented by the following formula:

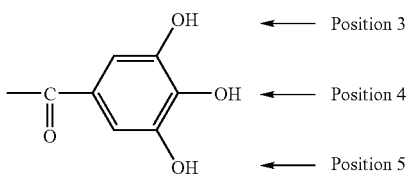

Besides, it is desirable to avoid the use of chemically synthesized compounds in food products. For these reasons, enzymes are needed that can effectively synthesize methylated catechins in a site specific manner.

[Patent Document 1] Japanese Patent Laid-Open Publication No. 2000-159670
[Patent Document 2] Japanese Patent Laid-Open Publication No. Sho 61-145177
[Patent Document 3] Japanese Patent Laid-Open Publication No. 2002-255810
[Non-Patent Document 1] Sano M, Suzuki M, Miyase T, Yoshino K, Maeda-Yamamoto M: J. Agric. Food Chem. 47(5) (1999): 1906-1910
[Non-Patent Document 2] Matsuo, N. et al., Allergy 52 (1997): 58-64
[Non-Patent Document 3] J. Biochem. 55 (1964): 205

DISCLOSURE OF THE INVENTION

Problems to be Solved by the Invention

Accordingly, it is an object of the present invention to provide a gene encoding a methylated catechin synthase that can effectively synthesize a methylated catechin, a compound having high antiallergic activity. It is another objective of the present invention to provide a plasmid that incorporates such a gene. It is still another object of the present invention to provide a transformed organism with the plasmid. It is yet another object of the present invention to provide a method for producing a methylated catechin synthase using the transformed organism. It is yet another object of the present invention to provide a method for producing a methylated catechin using the methylated catechin synthase obtained by the above production method.

Means for Solving the Problems

In an attempt to achieve these objects, the present inventors isolated a gene encoding a methylated catechin synthase from the leaves of Benifuki, one of the tea cultivars containing methylate catechins, and introduced this gene into *E. coli* to produce the methylated catechin synthase. Specifically, the present invention concerns the following:

(1) A gene encoding an enzyme that synthesizes at least one methylated catechin selected from the group consisting of an epigallocatechin-3-O-gallate derivative represented by the following general formula (I):

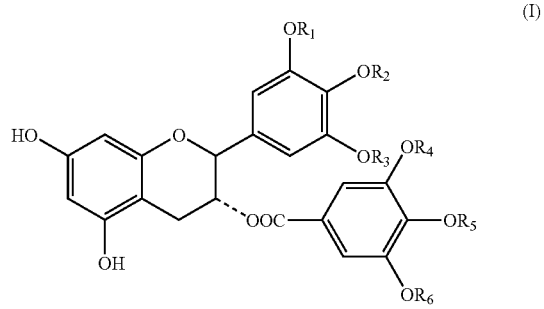

(wherein $R_1$ through $R_6$ are each a hydrogen atom or a methyl group and at least one of $R_1$ through $R_6$ is a methyl group], an epicatechin-3-O-gallate derivative represented by the following general formula (II):

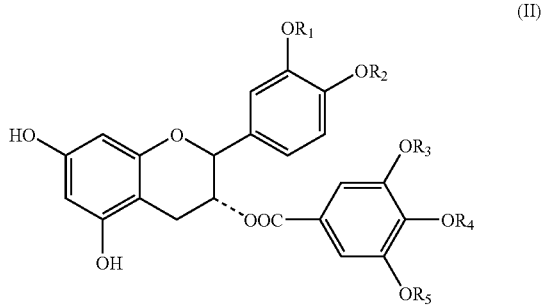

[wherein $R_1$ through $R_5$ are as defined above and at least one of $R_1$ through $R_5$ is a methyl group] and isomers thereof, the gene containing at least one nucleotide sequence selected from the group consisting of SEQ ID NOs: 1, 3 and 5.

(2) A gene encoding an enzyme that has an enzymatic activity to synthesize at least one methylated catechin selected from the group consisting of an epigallocatechin-3-O-gallate derivative represented by the following general formula (I):

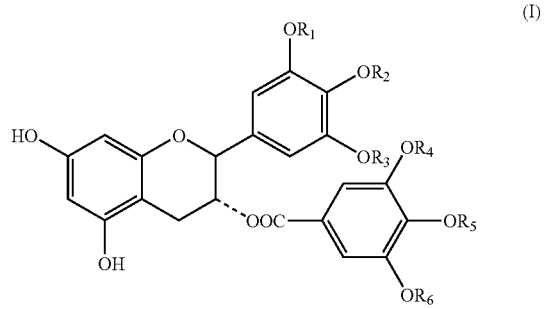

(wherein $R_1$ through $R_6$ are each a hydrogen atom or a methyl group and at least one of $R_1$ through $R_6$ is a methyl group], an epicatechin-3-O-gallate derivative represented by the following general formula (II):

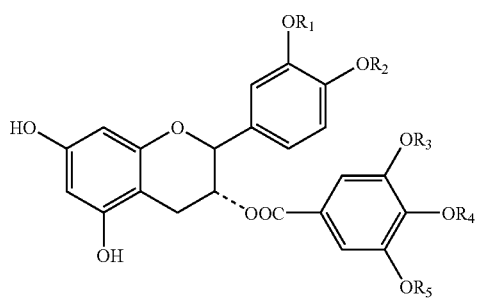

(II)

[wherein $R_1$ through $R_5$ are as defined above and at least one of $R_1$ through $R_5$ is a methyl group] and isomers thereof, the enzyme having an amino acid sequence resulting from insertion, addition, deletion or substitution of one or more amino acid residues in at least one amino acid sequence selected from the group consisting of SEQ ID NOs: 2, 4 and 6.

(3) A gene encoding a synthase that has an activity to synthesize at least one methylated catechin selected from the group consisting of an epigallocatechin-3-O-gallate derivative represented by the following general formula (I):

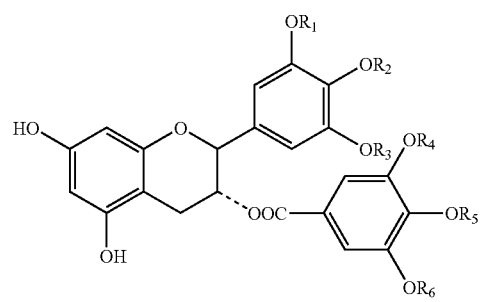

(I)

(wherein $R_1$ through $R_6$ are each a hydrogen atom or a methyl group and at least one of $R_1$ through $R_6$ is a methyl group], an epicatechin-3-O-gallate derivative represented by the following general formula (II):

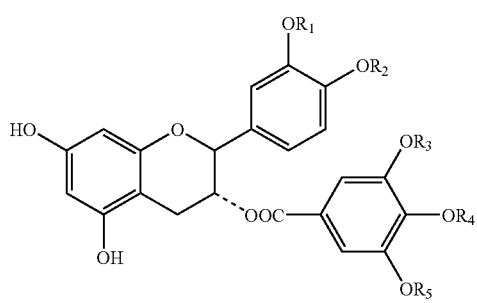

(II)

[wherein $R_1$ through $R_5$ are as defined above and at least one of $R_1$ through $R_5$ is a methyl group] and isomers thereof, the gene having 70% or higher homology to at least one nucleotide sequence selected from the group consisting of SEQ ID NOs: 1, 3 and 5.

(4) A recombinant expression vector incorporating the gene according to any one of (1) to (3).

(5) A transformed organism with the recombinant expression vector according to (4).

(6) The transformed organism according to (5), being a microorganism.

(7) The transformed organism according to (5), being a plant cell, plant tissue or plant body.

(8) A process for producing an enzyme that synthesizes at least one methylated catechin selected from the group consisting of an epigallocatechin-3-O-gallate derivative represented by the following general formula (I):

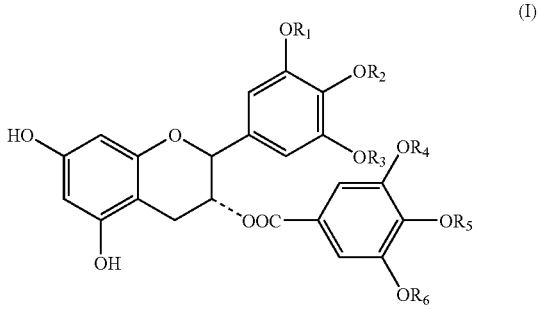

(I)

(wherein $R_1$ through $R_6$ are each a hydrogen atom or a methyl group and at least one of $R_1$ through $R_6$ is a methyl group], an epicatechin-3-O-gallate derivative represented by the following general formula (II):

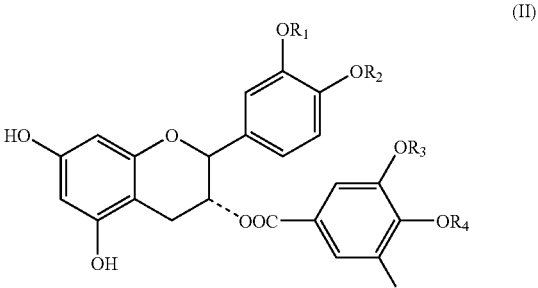

(II)

[wherein $R_1$ through $R_5$ are as defined above and at least one of $R_1$ through $R_5$ is a methyl group] and isomers thereof, the process comprising:

culturing the transformed organism according to any one of (6) and (7) to allow the transformed organism to produce the enzyme in the culture;

isolating the enzyme from the culture; and purifying the enzyme.

(9) A method for producing at least one methylated catechin selected from the group consisting of an epigallocatechin-3-O-gallate derivative represented by the following general formula (I):

(I)

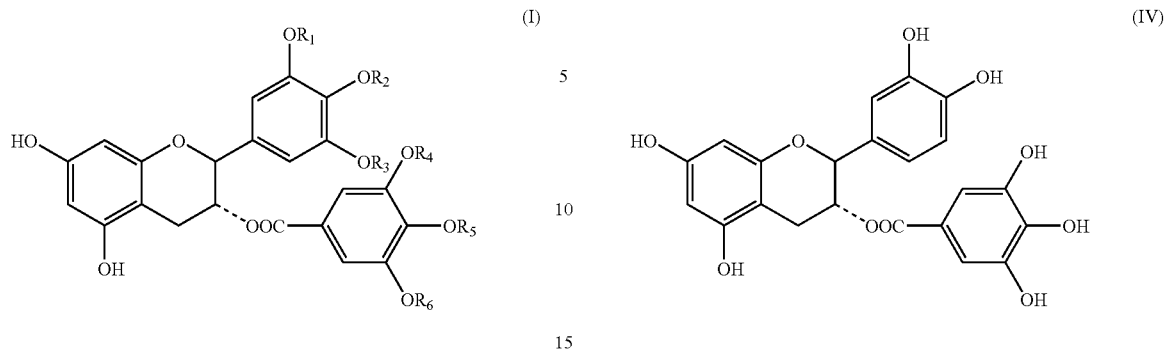

(wherein $R_1$ through $R_6$ are each a hydrogen atom or a methyl group and at least one of $R_1$ through $R_6$ is a methyl group], an epicatechin-3-O-gallate derivative represented by the following general formula (II):

(II)

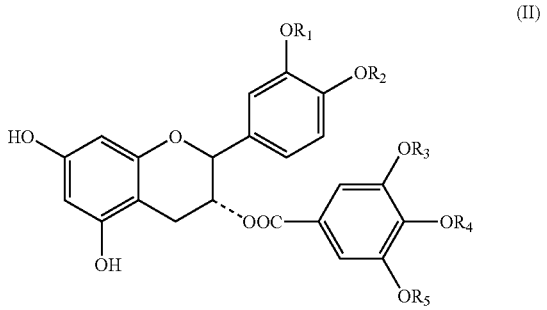

[wherein $R_1$ through $R_5$ are as defined above and at least one of $R_1$ through $R_5$ is a methyl group] and isomers thereof, the process comprising:

culturing the transformed organism according to any one of (6) and (7) to allow the transformed organism to produce methylated catechin synthase in the culture;

isolating the methylated catechin synthase from the culture; and reacting the methylated catechin synthase with at least one substrate selected from the group consisting of epigallocatechin-3-O-gallate represented by the following chemical formula (III):

(III)

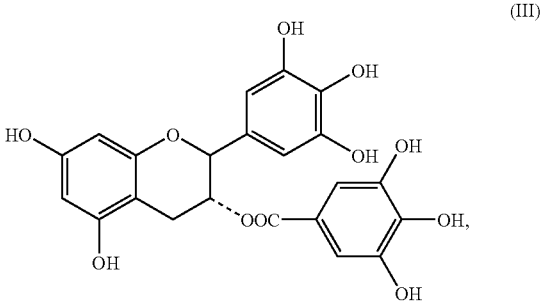

epicatechin-3-O-gallate represented by the following chemical formula (IV):

(IV)

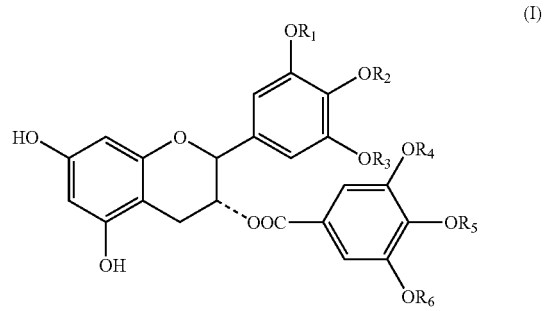

and isomers thereof.

EFFECT OF THE INVENTION

The methylated catechin synthase produced by the methylated catechin synthase gene of the present invention can utilize catechins, such as EGCG, as substrates to effectively produce methylated catechins, compounds that have high antiallergic activity, anticancer activity, antiobesity activity, antiarteriosclerosis activity, antihypertensive activity and antimicrobial activity.

BEST MODE FOR CARRYING OUT THE INVENTION

Figure 1:
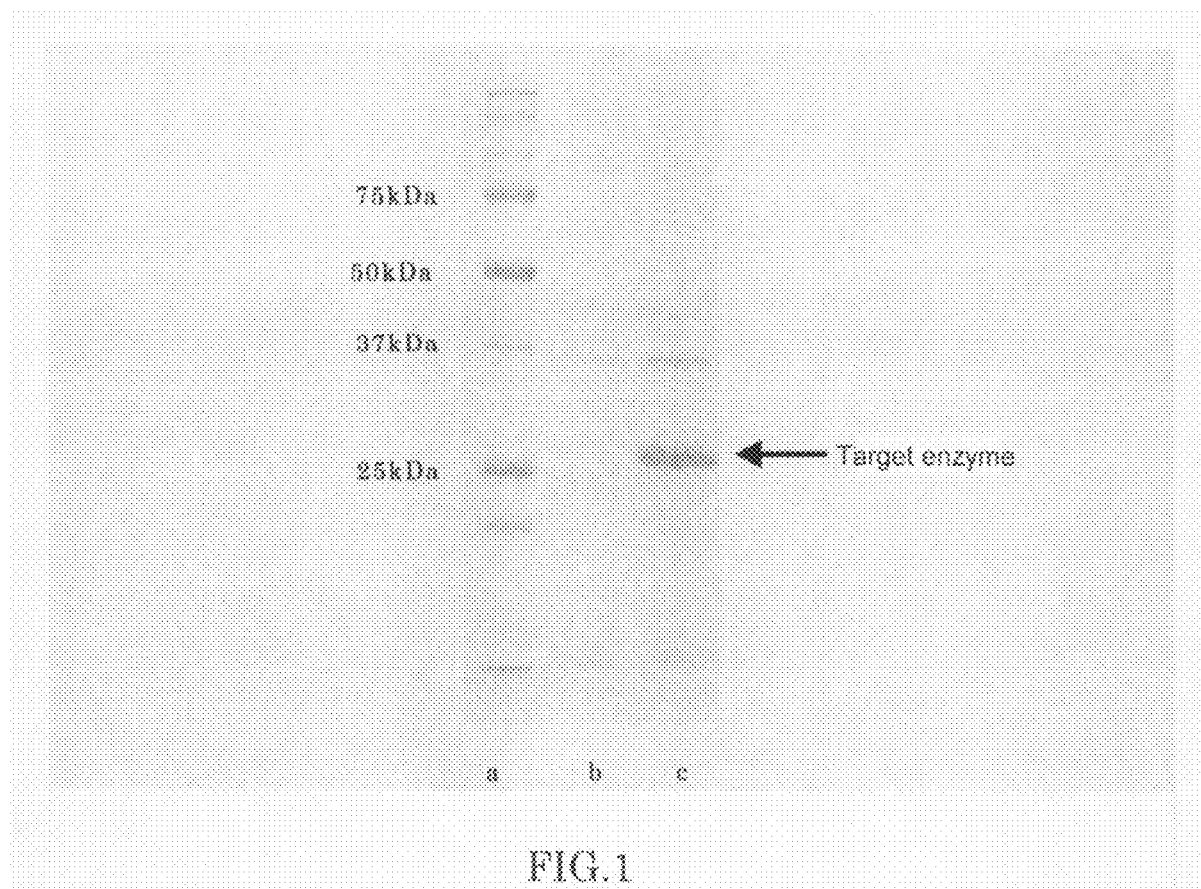
FIG. 1 shows the results of electrophoresis (SDS-PAGE) of an induced enzyme (lane a=molecular weight marker, lane b=before induction, lane c=after induction).

The term "methylated catechin" as used herein means at least one selected from the group consisting of epigallocatechin-3-O-gallate derivatives represented by the following general formula (I):

(I)

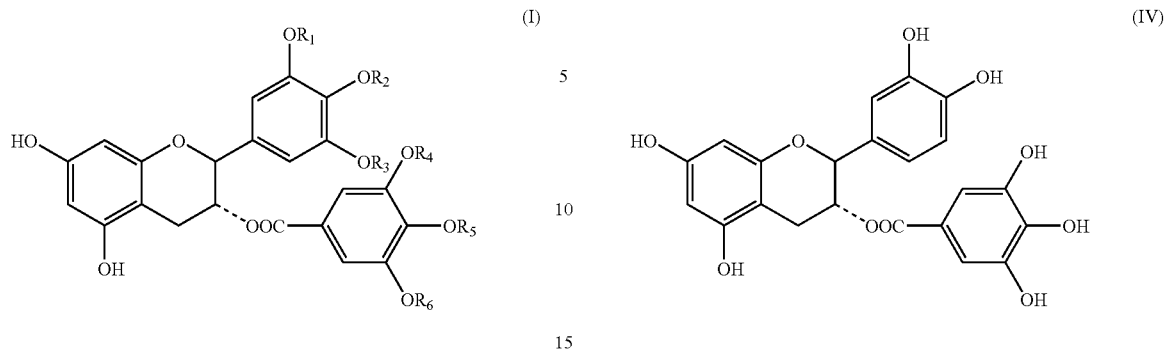

(wherein $R_1$ through $R_6$ are each a hydrogen atom or a methyl group and at least one of $R_1$ through $R_6$ is a methyl group], epicatechin-3-O-gallate derivatives represented by the following general formula (II):

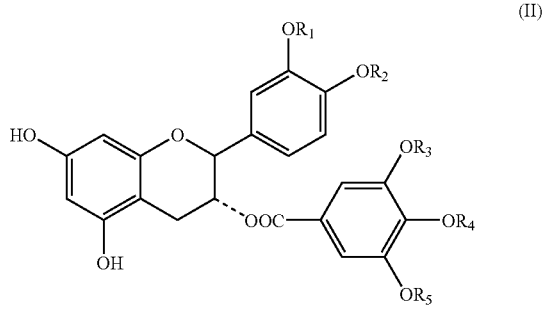

(II)

[wherein $R_1$ through $R_5$ are as defined above and at least one of $R_1$ through $R_5$ is a methyl group] and isomers thereof.

Specific examples of methylated catechins in accordance with the present invention include epigallocatechin-3-O-(3-O-methyl)gallate, epigallocatechin-3-O-(4-O-methyl)gallate, epigallocatechin-3-O-(3,5-O-dimethyl)gallate, epigallocatechin-3-O-(3,4-O-dimethyl)gallate, epicatechin-3-O-(3-O-methyl)gallate, epicatechin-3-O-(4-O-methyl)gallate, epicatechin-3-O-(3,5-O-dimethyl)gallate, epicatechin-3-O-(3,4-O-dimethyl)gallate and epi(3-O-methyl)gallocatechin-3-O-gallate.

The enzyme of the present invention for synthesizing methylated catechins (which may be referred to as "methylated catechin synthase," hereinafter) is an enzyme that utilizes a substrate selected from the group consisting of epigallocatechin-3-O-gallate, epicatechin-3-O-gallate and isomers thereof, to produce at least one methylated catechin selected from the group consisting of those represented by the general formulas (I) and (II) and isomers thereof.

The genetic recombination techniques used in the present invention are common techniques and are described in, for example, Molecular Cloning (Cold Spring Harbor Laboratory Press).

To obtain a target gene of methylated catechin synthase, total RNA is extracted from flavonoid-containing plants, preferably from tea, and more preferably from methylated catechin-containing tea cultivars, such as Seishin dai-pan, Benihomare, Benifuji and Benifuki. The total RNA is then subjected to RT-PCR using degenerate primers to obtain gene fragments as candidates for the target gene.

The gene encoding methylated catechin synthase in accordance with the present invention has at least one nucleotide sequence selected from the group consisting of SEQ ID NOs: 1, 3, and 5.

The gene of the present invention may have 70% or higher homology to at least one nucleotide sequence selected from the group consisting of SEQ ID NOs: 1, 3, and 5 and encode any synthase that has an activity to synthesize methylated catechins. The gene may have 70% or less homology to these base sequences as long as it has the activity to synthesize methylated catechins.

The candidate gene fragments for the target gene are cloned into any suitable vector that can be sequenced. For example, the vector may be a family of pUC vectors or a family of pGEM vectors that incorporates the DNA or RNA molecule for the desired gene. The resulting gene fragments are sequenced and RACE-PCR is performed based on the nucleotide sequence to obtain the full length gene.

The gene so obtained is then integrated into an expression vector. The vector may be any suitable vector that expresses a protein. For example, the vector may be a family of pET vectors or a family of pQE vectors that incorporates the DNA or RNA molecule for the desired gene. The expression vector is then introduced into a suitable host to express the desired protein.

The host that can be introduced the vector may be a plant cell, plant tissue, plant body or microorganism. Examples of the microorganism include *E. coli*, yeast, genus *Bacillus* and molds. The transformed hosts acquire the ability to enzymatically synthesize methylated catechins.

The methylated catechin synthase of the present invention encoded by at least one nucleotide sequence selected from the group consisting of SEQ ID NOs: 1, 3 and 5 has at least one amino acid sequence selected from the group consisting of SEQ ID NOs: 2, 4, and 6.

The transformed organism so obtained is then cultured under optimum conditions for the growth of the organism. For example, when the expression vector introduced into the host is induced by IPTG, the compound is added to the growth medium to induce the expression of the desired enzyme protein.

The gene of the present invention may be any gene encoding an amino acid resulting from insertion, addition, deletion or substitution of one or more amino acid residues in at least one amino acid sequence selected from the group consisting of SEQ ID NOs: 2, 4 and 6. Alternatively, the gene of the present invention may be any gene encoding an enzyme that has enzymatic activity to synthesize methylated catechins.

The organism used to make transformed organisms may be of the type that produces the desired enzyme within the cells or of the type that releases the enzyme from the cells. The latter type is preferred. The organisms that release the enzyme from the cells can be removed from the culture by centrifugation to obtain the desired enzyme as a crude product. The organisms that produce the enzyme within the cells may be sonicated or treated with lysozyme to break up cells and thus obtain the desired enzyme as a crude product. While the crude enzyme may be used in the methylation of catechins without further processing, it is preferably purified by molecular weight fractionation or other suitable techniques.

The purified enzyme is suspended in a buffer having a pH of 4.5 to 8.5, preferably 6.5 to 8. To this suspension, EGCG or ECG is added along with S-adenosyl-L-methionine (SAM) and the reaction is allowed to proceed at 5 to 60° C., preferably at 20 to 40° C., to form a methylated catechin.

EXAMPLES

The present invention will now be described in further detail with reference to examples, which are not intended to limit the scope of the invention in any way.

Example 1

Extraction of Total RNA from Benifuki

Benifuki tea leaves (1 g) were ground in liquid nitrogen and total RNA was extracted. Degenerate primers as shown below were designed and the total RNA (2 µg) was amplified in RT-PCR using the primers.

```
5'-degenerate primer:    CAGTAYATWYTNGARACHAGTGT
3'-degenerate primer:    TGTGRGCAACDCCRGCTTTYTBAAT (Sequence codes: Y = C, T; W = A, T; R = A, G;
N = A, C, G, T)
H = A, T, C; D = G, A, T; B = G, T, C; and
```

The RT-PCR product was confirmed by agarose gel electrophoresis and the amplified cDNA bands were purified from the agarose gel. The cDNA was cloned into pGEM-T vector (Promega) and the vector was introduced into E. coli strain JM-109 (Takara). The resulting JM-109 strain was cultured overnight in LB medium at 37° C. with shaking. Subsequently, the plasmid was extracted and the insert cDNA was sequenced.

Example 2

Isolation of Full-Length Gene

Specific primers were designed based on the nucleotide sequence of the isolated gene. Using the primers, 5'- and 3'-RACE PCRs were performed to obtain the full-length cDNA. The resulting PCR products were separated by agarose gel electrophoresis and the amplified bands were purified from the gel. The purified cDNA was cloned into pGEM-T vector and was sequenced. In this manner, the full-length gene of the desired enzyme protein was isolated.

5'- and 3'-primers were then designed based on the nucleotide sequence of the full-length gene. Using these primers, RT-PCR was performed on the total RNA (3 μg) to isolate the full-length gene of the desired enzyme. The resulting PCR products were separated by agarose gel electrophoresis and the amplified bands were purified from the gel. The purified cDNA was cloned into pGEM-T vector. The vector was introduced into E. coli strain JM109 and the cDNA was sequenced again. The nucleotide sequence and deduced amino acid sequence are shown in the sequence listing.

Example 3

Induction of Enzyme Protein Expression

The pGEM-T vector containing the gene insert for the desired enzyme protein and restriction sites for restriction enzymes NdeI and BamHI, introduced by primers during RT-PCR, was digested with NdeI and BamHI. The digested DNA was subjected to agarose gel electrophoresis to purify the gene insert. A pET28a(+) vector (Novagen) was also digested with NdeI and BamHI, subjected to agarose gel electrophoresis, and purified from the gel. The insert was cloned into the pET28a(+) vector between NdeI and BamHI sites and the vector was introduced into E. coli strain BL21 (DE3) (Stratagene). The resulting BL21(DE3) strain was cultured overnight in LB medium at 37° C. with shaking. Subsequently, part of the culture was transferred to new LB medium and cultured again. IPTG was then added to the culture to a final concentration of 1 mM and the cells were cultured at 28° C. with shaking to induce the enzyme. The culture was then centrifuged (7,000 rpm×10 min, 4° C.) to harvest the cells. The cell pellet was suspended in 20 mM PBS (pH 7.4) containing 1 mM DTT. The cell suspension was sonicated to break up cells and was centrifuged again (7,500 rpm×10 min, 4° C.). The supernatant was filtered through a 0.45 μm filter and the filtrate was used as the crude enzyme solution. The crude enzyme solution was subjected to 12% SDS-PAGE electrophoresis and the resulting band patterns were compared with those obtained by SDS-PAGE for non-induced E. coli: A band was observed for the induced cells at about 27 kDa, indicating the expression of the desired enzyme protein. The molecular weight of the enzyme protein determined from deduced amino acid sequence was 27.6 kDa. The results of electrophoresis for the induced enzyme protein are shown in FIG. 1.

Example 4

Enzymatic Reaction

Conversion of catechin to methylated catechin was carried out by using the crude enzyme solution in the following reaction system:

100 mM Tris-HCl (pH 6.8)
0.2 mM MgCl$_2$
25 μM EGCG or ECG
80 μM S-adenosyl-L-methionine (SAM)
Total volume 5 ml The reaction was allowed to proceed at 30° C. for 1 hour and was then terminated by the addition of 1N HCl (200 μl). Subsequently, 8 mL ethyl acetate was added and the reaction mixture was shaken. The organic phase was collected after centrifugation (3000 G, 5 min) and 1% ascorbic acid (200 μl) was added to it. This mixture was vacuum-concentrated and analyzed by HPLC for the production of the following methylated catechins: epigallocatechin-3-O-(3-O-methyl)gallate, epigallocatechin-3-O-(4-O-methyl)gallate, epigallocatechin-3-O-(3,5-O-dimethyl)gallate, epigallocatechin-3-O-(3,4-O-dimethyl)gallate, epicatechin-3-O-(3-O-methyl)gallate, epicatechin-3-O-(4-O-methyl)gallate, epicatechin-3-O-(3,5-O-dimethyl)gallate, epicatechin-3-O-(3,4-O-dimethyl)gallate and epi(3-O-methyl)gallocatechin-3-O-gallate. The results indicate that each of epigallocatechin-3-O-(3-O-methyl)gallate, epigallocatechin-3-O-(4-O-methyl)gallate, epigallocatechin-3-O-(3,5-O-dimethyl)gallate, epigallocatechin-3-O-(3,4-O-dimethyl)gallate, epicatechin-3-O-(3-O-methyl)gallate, epicatechin-3-O-(4-O-methyl)gallate, epicatechin-3-O-(3,5-O-dimethyl)gallate, epicatechin-3-O-(3,4-O-dimethyl)gallate and epi(3-O-methyl)gallocatechin-3-O-gallate was produced and their amounts were dependent upon the amount of the crude enzyme used (Table 1). None of the methylated catechins was not formed when epigallocatechin-3-O-gallate (EGCG), epicatechin-3-O-gallate (ECG) or S-adenosyl-L-methionine (SAM) was eliminated from the reaction system.

These results indicate that an enzyme having an activity to synthesize methylated catechins was obtained.

TABLE 1

Amounts of methylated catechins produced by enzymatic reaction (μg/ml)

| | Amount of enzyme added (ml) | | | | | |
|---|---|---|---|---|---|---|
| | 0 | 0.05 | 0.1 | 0.5 | 1.0 | 2.0 |
| epigallocatechin-3-O-(3-O-methyl)gallate | 0 | 0.8 | 2.8 | 9.9 | 32.9 | 45.4 |
| epigallocatechin-3-O-(4-O-methyl)gallate | 0 | 0.2 | 0.3 | 0.6 | 2.6 | 5.7 |
| epigallocatechin-3-O-(3,5-O-dimethyl)gallate | 0 | 0.3 | 1.3 | 2.2 | 14.1 | 44.9 |
| epigallocatechin-3-O-(3,4-O-dimethyl)gallate | 0 | 0.1 | 0.4 | 0.9 | 5.1 | 21.3 |
| epicatechin-3-O-(3-O-methyl)gallate | 0 | 0.7 | 2.4 | 1.2 | 30.1 | 42.2 |
| epicatechin-3-O-(4-O-methyl)gallate | 0 | 0.2 | 0.4 | 0.9 | 2.9 | 4.8 |
| epicatechin-3-O-(3,5-O-dimethyl)gallate | 0 | 0.2 | 1.6 | 2.8 | 12.5 | 49.6 |
| epicatechin-3-O-(3,4-O-dimethyl)gallate | 0 | 0.1 | 0.2 | 0.7 | 3.8 | 16.6 |
| epi(3-O-methyl)gallocatechin-3-O-gallate | 0 | 0.6 | 2.2 | 8.3 | 26.3 | 38.1 |

INDUSTRIAL APPLICABILITY

The methylated catechin synthase produced by the methylated catechin synthase gene of the present invention can utilize EGCG and other catechins as substrates to effectively produce methylated catechins, compounds having high antiallergic activity. The present invention therefore is of significant importance.

(Sequence Listing)

The invention claimed is:
1. An isolated gene encoding an enzyme that catalyzes the synthesis of at least one methylated catechin selected from the group consisting of:
   a) an epigallocatechin-3-O-gallate derivative represented by the following general formula (I):

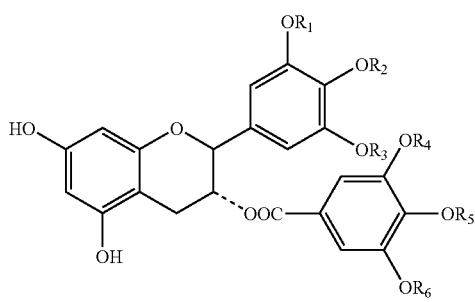

wherein $R_1$ through $R_6$ are each a hydrogen atom or a methyl group and at least one of $R_1$ through $R_6$ is a methyl group,
   b) an epicatechin-3-O-gallate derivative represented by the following general formula (II):

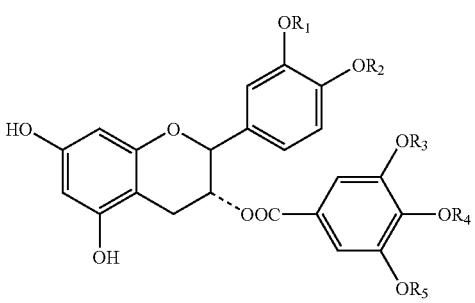

wherein $R_1$ through $R_5$ are as defined above and at least one of $R_1$ through $R_5$ is a methyl group and
   c) isomers thereof,
wherein the gene contains a nucleotide sequence selected from the group consisting of SEQ ID NOs: 1, 3 and 5.

2. An isolated gene encoding an enzyme that catalyzes the synthesis of at least one methylated catechin selected from the group consisting of:
   a) an epigallocatechin-3-O-gallate derivative represented by the following general formula (I):

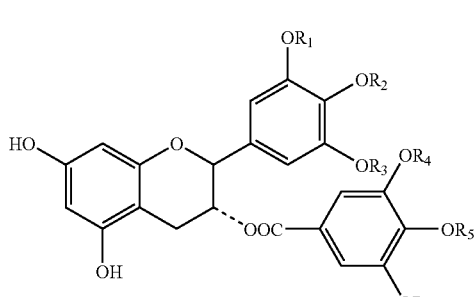

wherein $R_1$ through $R_6$ are each a hydrogen atom or a methyl group and at least one of $R_1$ through $R_6$ is a methyl group,
   b) an epicatechin-3-O-gallate derivative represented by the following general formula (II):

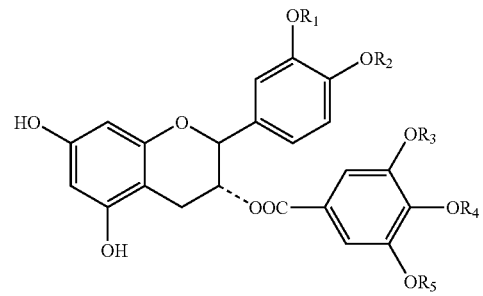

wherein $R_1$ through $R_5$ are as defined above and at least one of $R_1$ through $R_5$ is a methyl group and
   c) isomers thereof,
wherein the enzyme has an amino acid sequence selected from the group consisting of SEQ ID NOs: 2, 4 and 6.

3. A recombinant expression vector comprising the gene of claim 1 or 2.

4. An isolated host cell comprising the recombinant expression vector according to claim 3.

5. A transformed organism comprising the recombinant expression of vector of claim 3, wherein said organism is a plant cell, plant tissue or plant body.

6. A process for producing an enzyme that catalyzes the synthesis of at least one methylated catechin selected from the group consisting of:
   a) an epigallocatechin-3-O-gallate derivative represented by the following general formula (I):

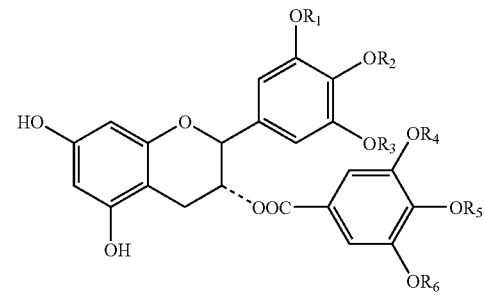

wherein $R_1$ through $R_6$ are each a hydrogen atom or a methyl group and at least one of $R_1$ through $R_6$ is a methyl group,
   b) an epicatechin-3-O-gallate derivative represented by the following general formula (II):

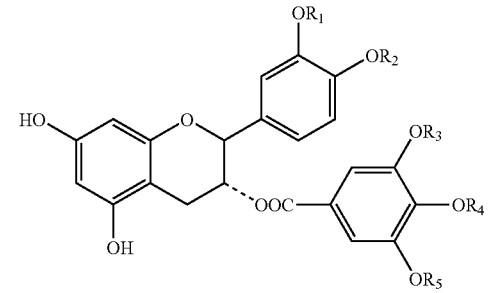

wherein $R_1$ through $R_5$ are as defined above and at least one of $R_1$ through $R_5$ is a methyl group and
 c) isomers thereof,
  the process comprising:
   culturing the transformed organism according to claim 5 to allow the transformed organism to produce the enzyme in the culture;
   isolating the enzyme from the culture; and
   purifying the enzyme.

7. A method for producing at least one methylated catechin selected from the group consisting of:
 a) an epigallocatechin-3-O-gallate derivative represented by the following general formula (I):

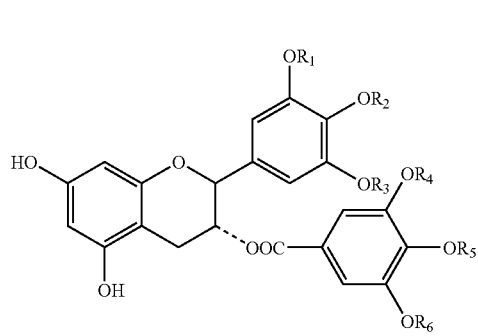

wherein $R_1$ through $R_6$ are each a hydrogen atom or a methyl group and at least one of $R_1$ through $R_6$ is a methyl group,
 b) an epicatechin-3-O-gallate derivative represented by the following general formula (II):

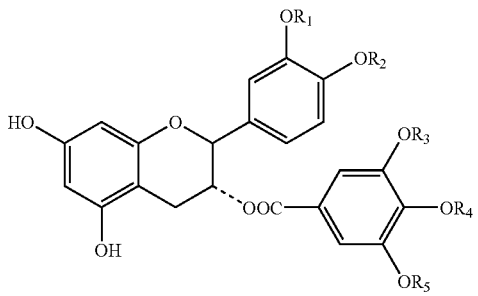

wherein $R_1$ through $R_5$ are as defined above and at least one of $R_1$ through $R_5$ is a methyl group and
 c) isomers thereof,
  the process comprising:
   culturing the transformed organism according to claim 5 to allow the transformed organism to produce methylated catechin synthase in the culture;
   isolating the methylated catechin synthase from the culture; and
   reacting the methylated catechin synthase with at least one substrate selected from the group consisting of:
 a) epigallocatechin-3-O-gallate represented by the following chemical formula (III):

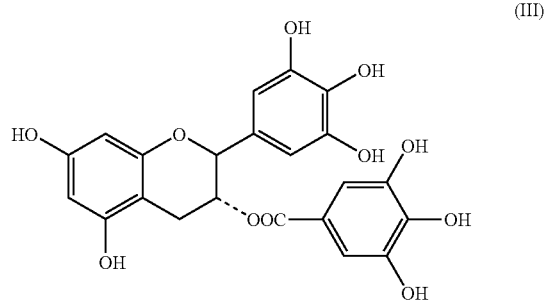

b) epicatechin-3-O-gallate represented by the following chemical formula (IV):

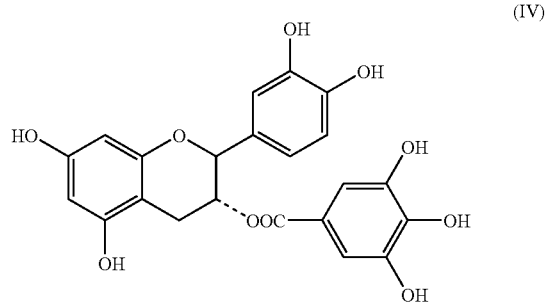

and c) isomers thereof.

* * * * *

```
SEQUENCE LISTING

<160> NUMBER OF SEQ ID NOS: 6

<210> SEQ ID NO 1
<211> LENGTH: 1094
<212> TYPE: DNA
<213> ORGANISM: Camellia sinensis
<220> FEATURE:
<223> OTHER INFORMATION: Inventor:Mari Yamamoto
<223> OTHER INFORMATION: Inventor:Masanobu Kirita
<223> OTHER INFORMATION: Inventor:Manabu Sami
<220> FEATURE:
<223> OTHER INFORMATION: Inventor:Mitsuo Ikeda
<220> FEATURE:
<221> NAME/KEY: CDS
<222> LOCATION: (84)..(818)
<223> OTHER INFORMATION:

<400> SEQUENCE: 1
ctctctctgc tcaccggcga tccaacactc cggcgaaaca aaaccaaaga ggaaaaaaca      60
cagaaaatta attcgctgca ata atg gca aca aac gga gaa gga gaa cag aat     113
                         Met Ala Thr Asn Gly Glu Gly Glu Gln Asn
                          1               5                  10 ctc agg cac caa gag gtc ggc cac aag agt ctt tta cag agc gat gct        161
Leu Arg His Gln Glu Val Gly His Lys Ser Leu Leu Gln Ser Asp Ala
                15                  20                  25 ctc tac cag tat ata ctt gag acc agt gtt tac cca aga gag cca gag        209
Leu Tyr Gln Tyr Ile Leu Glu Thr Ser Val Tyr Pro Arg Glu Pro Glu
            30                  35                  40 gcg atg aag gag ctc aga gag gtc act gca aaa cat cca tgg aac atc        257
Ala Met Lys Glu Leu Arg Glu Val Thr Ala Lys His Pro Trp Asn Ile
        45                  50                  55 atg act acc tct gcc gac gaa ggt cag ttc ttg aac atg ctt ttg aag        305
Met Thr Thr Ser Ala Asp Glu Gly Gln Phe Leu Asn Met Leu Leu Lys
    60                  65                  70 ctt atc aac gcc aag aac acc atg gaa atc ggt gtt tac act ggt tac        353
Leu Ile Asn Ala Lys Asn Thr Met Glu Ile Gly Val Tyr Thr Gly Tyr
75                  80                  85                  90
```

```
tct ctt ctc gcc acc gcc ctt gct ctc ccc gat gat ggg aag att ttg      401
Ser Leu Leu Ala Thr Ala Leu Ala Leu Pro Asp Asp Gly Lys Ile Leu
            95                  100                 105 gca atg gac att aac aga gaa aac ttc gaa atc ggt ctg ccg ata att      449
Ala Met Asp Ile Asn Arg Glu Asn Phe Glu Ile Gly Leu Pro Ile Ile
        110                 115                 120 gaa aag gcc ggc gtc gct cac aaa atc gac ttc aga gaa ggc cct gct      497
Glu Lys Ala Gly Val Ala His Lys Ile Asp Phe Arg Glu Gly Pro Ala
                125                 130                 135 ctg cct gct ctc gat caa atg atc gaa gat gga aag cat cat ggg tcg      545
Leu Pro Ala Leu Asp Gln Met Ile Glu Asp Gly Lys His His Gly Ser
    140                 145                 150 ttt gat ttc att ttc gtg gac gct gac aag gac aac tac atc aac tac      593
Phe Asp Phe Ile Phe Val Asp Ala Asp Lys Asp Asn Tyr Ile Asn Tyr
155                 160                 165                 170 cac aag agg ctg att gat ctg gtg aag gtt ggg gga ctg atc ggc tac      641
His Lys Arg Leu Ile Asp Leu Val Lys Val Gly Gly Leu Ile Gly Tyr
                175                 180                 185 gat aac acc ctc tgg aac ggc tct gtg gtg gcg cct ccg gac gct ccg      689
Asp Asn Thr Leu Trp Asn Gly Ser Val Val Ala Pro Pro Asp Ala Pro
        190                 195                 200 atg agg aag tac gta agg tac tac aga gac ttc gtc ttg gag ctc aac      737
Met Arg Lys Tyr Val Arg Tyr Tyr Arg Asp Phe Val Leu Glu Leu Asn
    205                 210                 215 aag gca ctc gcc gcc gat ccc cgc atc gag atc tgc atg ctt ccc gtc      785
Lys Ala Leu Ala Ala Asp Pro Arg Ile Glu Ile Cys Met Leu Pro Val
220                 225                 230 ggc gat ggc att acc ctg tgc cgg cgt gtc tgc tgattccaac ccattgctgg    838
Gly Asp Gly Ile Thr Leu Cys Arg Arg Val Cys
235                 240                 245 acaaaaacca aataatatga tattttgctt ttattttat tatctttgt tatgtcatat      898 gtatttgtat ttcaatgga cggtggatga ttggaagagt tcacgaccta cgcttccgat    958
ttgatttgct gctcgaatca acatacaaag tggtctatta attggttttg aaatattagt   1018
aatgttgttc atgcaatatt tttataaata tcaattcata attgaaaata tggggaaaaa   1078
aaaaaaaaaa aaaaaa                                                   1094

<210> SEQ ID NO 2
<211> LENGTH: 245
<212> TYPE: PRT
<213> ORGANISM: Camellia sinensis

<400> SEQUENCE: 2

Met Ala Thr Asn Gly Glu Gly Glu Gln Asn Leu Arg His Gln Glu Val
1               5                   10                  15

Gly His Lys Ser Leu Leu Gln Ser Asp Ala Leu Tyr Gln Tyr Ile Leu
            20                  25                  30

Glu Thr Ser Val Tyr Pro Arg Glu Pro Glu Ala Met Lys Glu Leu Arg
        35                  40                  45

Glu Val Thr Ala Lys His Pro Trp Asn Ile Met Thr Thr Ser Ala Asp
    50                  55                  60

Glu Gly Gln Phe Leu Asn Met Leu Leu Lys Leu Ile Asn Ala Lys Asn
65                  70                  75                  80

Thr Met Glu Ile Gly Val Tyr Thr Gly Tyr Ser Leu Leu Ala Thr Ala
                85                  90                  95

Leu Ala Leu Pro Asp Asp Gly Lys Ile Leu Ala Met Asp Ile Asn Arg
            100                 105                 110
```

```
Glu Asn Phe Glu Ile Gly Leu Pro Ile Ile Glu Lys Ala Gly Val Ala
            115                 120                 125

His Lys Ile Asp Phe Arg Glu Gly Pro Ala Leu Pro Ala Leu Asp Gln
        130                 135                 140

Met Ile Glu Asp Gly Lys His His Gly Ser Phe Asp Phe Ile Phe Val
145                 150                 155                 160

Asp Ala Asp Lys Asp Asn Tyr Ile Asn Tyr His Lys Arg Leu Ile Asp
                165                 170                 175

Leu Val Lys Val Gly Gly Leu Ile Gly Tyr Asp Asn Thr Leu Trp Asn
            180                 185                 190

Gly Ser Val Val Ala Pro Pro Asp Ala Pro Met Arg Lys Tyr Val Arg
        195                 200                 205

Tyr Tyr Arg Asp Phe Val Leu Glu Leu Asn Lys Ala Leu Ala Ala Asp
    210                 215                 220

Pro Arg Ile Glu Ile Cys Met Leu Pro Val Gly Asp Gly Ile Thr Leu
225                 230                 235                 240

Cys Arg Arg Val Cys
                245

<210> SEQ ID NO 3
<211> LENGTH: 1094
<212> TYPE: DNA
<213> ORGANISM: Camellia sinensis
<220> FEATURE:
<221> NAME/KEY: CDS
<222> LOCATION: (84)..(818)
<223> OTHER INFORMATION:

<400> SEQUENCE: 3
ctctctctgc tcaccggcga tccaacactc cggcgaaaca aaaccaaaga ggaaaaaaca    60
cagaaaatta attcgctgca ata atg gca aca aac gga gaa gga gaa cag aat   113
                         Met Ala Thr Asn Gly Glu Gly Glu Gln Asn
                           1               5                  10 ctc agg cac caa gag gtc ggc cac aag agt ctt tta cag agc gat gct     161
Leu Arg His Gln Glu Val Gly His Lys Ser Leu Leu Gln Ser Asp Ala
            15                  20                  25 ctc tac cag tat ata ctt gag acc agt gtt tac cca aga gag cca gag     209
Leu Tyr Gln Tyr Ile Leu Glu Thr Ser Val Tyr Pro Arg Glu Pro Glu
        30                  35                  40 gcg atg aag gag ctc aga gag gtc act gca aaa cat cca tgg aac atc     257
Ala Met Lys Glu Leu Arg Glu Val Thr Ala Lys His Pro Trp Asn Ile
    45                  50                  55 atg act acc tct gcc gac gaa ggt cag ttc ttg aac atg ctt ttg aag     305
Met Thr Thr Ser Ala Asp Glu Gly Gln Phe Leu Asn Met Leu Leu Lys
60                  65                  70 ctt atc aac gcc aag aac acg atg gaa atc ggt gtt tac act ggt tac     353
Leu Ile Asn Ala Lys Asn Thr Met Glu Ile Gly Val Tyr Thr Gly Tyr
75                  80                  85                  90 tct ctt cta gcc acc gcc ctt gct ctc ccc gat gat ggg aag att ttg     401
Ser Leu Leu Ala Thr Ala Leu Ala Leu Pro Asp Asp Gly Lys Ile Leu
                95                  100                 105 gca atg gac att aac aga gat aac ttc gaa atc ggt ctg ccg ata att     449
Ala Met Asp Ile Asn Arg Asp Asn Phe Glu Ile Gly Leu Pro Ile Ile
            110                 115                 120 gaa aag gcc ggc gtc gct cac aaa atc gac ttc aga gaa ggc cct gct     497
Glu Lys Ala Gly Val Ala His Lys Ile Asp Phe Arg Glu Gly Pro Ala
        125                 130                 135 ctg cct gct ctc gat aaa atg gtc gaa gat gga aag cat cat ggg tcg     545
```

```
Leu Pro Ala Leu Asp Lys Met Val Glu Asp Gly Lys His His Gly Ser
    140                 145                 150 ttt gat ttc att ttc gtg gac gct gac aag gac aac tac atc aac tac       593
Phe Asp Phe Ile Phe Val Asp Ala Asp Lys Asp Asn Tyr Ile Asn Tyr
155                 160                 165                 170 cac aag agg ctg att gat ctg gtg aag gtt ggg gga ctg atc ggc tac       641
His Lys Arg Leu Ile Asp Leu Val Lys Val Gly Gly Leu Ile Gly Tyr
                175                 180                 185 gat aac acc ctc tgg aac ggc tct gtg gtg gcg cct ccg gac gct ccg       689
Asp Asn Thr Leu Trp Asn Gly Ser Val Val Ala Pro Pro Asp Ala Pro
            190                 195                 200 atg agg aag tac gta agg tac tac aga gac ttc gtc ttg gag ctc aac       737
Met Arg Lys Tyr Val Arg Tyr Tyr Arg Asp Phe Val Leu Glu Leu Asn
        205                 210                 215 aag gca ctc gcc gcc gat ccc cgc atc gag atc tgc atg ctt cct gtc       785
Lys Ala Leu Ala Ala Asp Pro Arg Ile Glu Ile Cys Met Leu Pro Val
    220                 225                 230 ggc gat ggc att acc ctg tgc cgg cgt gtc tgc tgattccaac ccattgctgg     838
Gly Asp Gly Ile Thr Leu Cys Arg Arg Val Cys
235                 240                 245 acaaaaacca aataatatga tatttgctt ttatttttat tatctttgt tatgtcatat       898 gtatttgtat ttctaatgga cggtggatga ttggaagagt tcacgaccta cgcttccgat    958
ttgatttgct gctcgaatca acatacaaag tggtctatta attggttttg aaatattagt    1018
aatgttgttc atgcaatatt tttataaata tcaattcata attgaaaata tggggaaaaa    1078
aaaaaaaaaa aaaaaa                                                    1094

<210> SEQ ID NO 4
<211> LENGTH: 245
<212> TYPE: PRT
<213> ORGANISM: Camellia sinensis

<400> SEQUENCE: 4

Met Ala Thr Asn Gly Glu Gly Glu Gln Asn Leu Arg His Gln Glu Val
1               5                   10                  15

Gly His Lys Ser Leu Leu Gln Ser Asp Ala Leu Tyr Gln Tyr Ile Leu
            20                  25                  30

Glu Thr Ser Val Tyr Pro Arg Glu Pro Glu Ala Met Lys Glu Leu Arg
        35                  40                  45

Glu Val Thr Ala Lys His Pro Trp Asn Ile Met Thr Thr Ser Ala Asp
    50                  55                  60

Glu Gly Gln Phe Leu Asn Met Leu Leu Lys Leu Ile Asn Ala Lys Asn
65                  70                  75                  80

Thr Met Glu Ile Gly Val Tyr Thr Gly Tyr Ser Leu Leu Ala Thr Ala
                85                  90                  95

Leu Ala Leu Pro Asp Asp Gly Lys Ile Leu Ala Met Asp Ile Asn Arg
            100                 105                 110

Asp Asn Phe Glu Ile Gly Leu Pro Ile Ile Glu Lys Ala Gly Val Ala
        115                 120                 125

His Lys Ile Asp Phe Arg Glu Gly Pro Ala Leu Pro Ala Leu Asp Lys
    130                 135                 140

Met Val Glu Asp Gly Lys His His Gly Ser Phe Asp Phe Ile Phe Val
145                 150                 155                 160

Asp Ala Asp Lys Asp Asn Tyr Ile Asn Tyr His Lys Arg Leu Ile Asp
                165                 170                 175

Leu Val Lys Val Gly Gly Leu Ile Gly Tyr Asp Asn Thr Leu Trp Asn
```

-continued

```
                    180                 185                 190
Gly Ser Val Val Ala Pro Pro Asp Ala Pro Met Arg Lys Tyr Val Arg
            195                 200                 205
Tyr Tyr Arg Asp Phe Val Leu Glu Leu Asn Lys Ala Leu Ala Ala Asp
        210                 215                 220
Pro Arg Ile Glu Ile Cys Met Leu Pro Val Gly Asp Gly Ile Thr Leu
225                 230                 235                 240
Cys Arg Arg Val Cys
            245

<210> SEQ ID NO 5
<211> LENGTH: 1094
<212> TYPE: DNA
<213> ORGANISM: Camellia sinensis
<220> FEATURE:
<221> NAME/KEY: CDS
<222> LOCATION: (84)..(818)
<223> OTHER INFORMATION:

<400> SEQUENCE: 5
```

| | |
|---|---:|
| ctctctctgc tcaccggcga tccaacactc cggcgaaaca aaaccaaaga ggaaaaaaca | 60 |

| | | |
|---|---|---:|
| cagaaaatta attcgctgca ata atg gca aca aac gga gaa gga gaa cag aat<br>                                 Met Ala Thr Asn Gly Glu Gly Glu Gln Asn<br>                                  1               5               10 | | 113 |
| ctc agg cac caa gag gtc ggc cac aag agt ctt tta cag agc gat gct<br>Leu Arg His Gln Glu Val Gly His Lys Ser Leu Leu Gln Ser Asp Ala<br>               15                  20                25 | | 161 |
| ctc tac cag tat ata ctt gag acc agt gtt tac cca aga gag cca gag<br>Leu Tyr Gln Tyr Ile Leu Glu Thr Ser Val Tyr Pro Arg Glu Pro Glu<br>         30                  35                  40 | | 209 |
| gcg atg aag gag ctc aga gag gtc act gca aaa cat cca tgg aac atc<br>Ala Met Lys Glu Leu Arg Glu Val Thr Ala Lys His Pro Trp Asn Ile<br>       45                  50                55 | | 257 |
| atg act acc tct gcc gac gaa ggt cag ttc ttg aac atg ctt ttg aag<br>Met Thr Thr Ser Ala Asp Glu Gly Gln Phe Leu Asn Met Leu Leu Lys<br>60                  65                  70 | | 305 |
| ctt atc aac gcc aag aac acg atg gaa atc ggt gtt tac act ggt tac<br>Leu Ile Asn Ala Lys Asn Thr Met Glu Ile Gly Val Tyr Thr Gly Tyr<br>75                  80                85                90 | | 353 |
| tct ctt ctc gcc acc gcc ctt gct ctc ccc gat gat ggg aag att ttg<br>Ser Leu Leu Ala Thr Ala Leu Ala Leu Pro Asp Asp Gly Lys Ile Leu<br>               95                100              105 | | 401 |
| gca atg gac att aac aga gaa aac ttc gaa atc ggt ctg ccg ata att<br>Ala Met Asp Ile Asn Arg Glu Asn Phe Glu Ile Gly Leu Pro Ile Ile<br>        110                115                120 | | 449 |
| gaa aag gcc ggc gtc gct cac aaa atc gac ttc aga gaa ggc cct gct<br>Glu Lys Ala Gly Val Ala His Lys Ile Asp Phe Arg Glu Gly Pro Ala<br>       125               130                135 | | 497 |
| ctg cct gct ctc gat aaa atg gtc gaa gat gga aag cat cat ggg tcg<br>Leu Pro Ala Leu Asp Lys Met Val Glu Asp Gly Lys His His Gly Ser<br>    140                145                150 | | 545 |
| ttt gat ttc att ttc gtg gac gct gac aag gac aac tac atc aac tac<br>Phe Asp Phe Ile Phe Val Asp Ala Asp Lys Asp Asn Tyr Ile Asn Tyr<br>155                 160                165              170 | | 593 |
| cac aag agg ctg att gat ctg gtg aag gtt ggg gga ctg atc ggc tac<br>His Lys Arg Leu Ile Asp Leu Val Lys Val Gly Gly Leu Ile Gly Tyr<br>        175                180                185 | | 641 |
| gat aac acc ctc tgg aac ggc tct gtg gtg gcg cct ccg gac gct ccg<br>Asp Asn Thr Leu Trp Asn Gly Ser Val Val Ala Pro Pro Asp Ala Pro<br>    190                195                200 | | 689 |

```
atg agg aag tac gta agg tac tac aga gac ttc gtc ttg gag ctc aac      737
Met Arg Lys Tyr Val Arg Tyr Tyr Arg Asp Phe Val Leu Glu Leu Asn
    205                 210                 215 aag gca ctc gcc gcc gat ccc cgc atc gag atc tgc atg ctt cct gtc      785
Lys Ala Leu Ala Ala Asp Pro Arg Ile Glu Ile Cys Met Leu Pro Val
220                 225                 230 ggc gat ggc att acc ctg tgc cgg cgt gtc tgc tgattccaac ccattgctgg    838
Gly Asp Gly Ile Thr Leu Cys Arg Arg Val Cys
235                 240                 245 acaaaaacca aataatatga tattttgctt ttattttat tatcttttgt tatgtcatat      898
gtatttgtat ttctaatgga cggtggatga ttggaagagt tcacgaccta cgcttccgat    958
ttgatttgct gctcgaatca acatacaaag tggtctatta attggttttg aaatattagt   1018
aatgttgttc atgcaatatt tttataaata tcaattcata attgaaaata tggggaaaaa   1078
aaaaaaaaaa aaaaa                                                    1094
```

<210> SEQ ID NO 6
<211> LENGTH: 245
<212> TYPE: PRT
<213> ORGANISM: Camellia sinensis

<400> SEQUENCE: 6

```
Met Ala Thr Asn Gly Glu Gly Glu Gln Asn Leu Arg His Gln Glu Val
1               5                   10                  15

Gly His Lys Ser Leu Leu Gln Ser Asp Ala Leu Tyr Gln Tyr Ile Leu
            20                  25                  30

Glu Thr Ser Val Tyr Pro Arg Glu Pro Glu Ala Met Lys Glu Leu Arg
        35                  40                  45

Glu Val Thr Ala Lys His Pro Trp Asn Ile Met Thr Thr Ser Ala Asp
    50                  55                  60

Glu Gly Gln Phe Leu Asn Met Leu Leu Lys Leu Ile Asn Ala Lys Asn
65                  70                  75                  80

Thr Met Glu Ile Gly Val Tyr Thr Gly Tyr Ser Leu Leu Ala Thr Ala
                85                  90                  95

Leu Ala Leu Pro Asp Asp Gly Lys Ile Leu Ala Met Asp Ile Asn Arg
            100                 105                 110

Glu Asn Phe Glu Ile Gly Leu Pro Ile Ile Glu Lys Ala Gly Val Ala
        115                 120                 125

His Lys Ile Asp Phe Arg Glu Gly Pro Ala Leu Pro Ala Leu Asp Lys
    130                 135                 140

Met Val Glu Asp Gly Lys His His Gly Ser Phe Asp Phe Ile Phe Val
145                 150                 155                 160

Asp Ala Asp Lys Asp Asn Tyr Ile Asn Tyr His Lys Arg Leu Ile Asp
                165                 170                 175

Leu Val Lys Val Gly Gly Leu Ile Gly Tyr Asp Asn Thr Leu Trp Asn
            180                 185                 190

Gly Ser Val Val Ala Pro Pro Asp Ala Pro Met Arg Lys Tyr Val Arg
        195                 200                 205

Tyr Tyr Arg Asp Phe Val Leu Glu Leu Asn Lys Ala Leu Ala Ala Asp
    210                 215                 220

Pro Arg Ile Glu Ile Cys Met Leu Pro Val Gly Asp Gly Ile Thr Leu
225                 230                 235                 240

Cys Arg Arg Val Cys
            245
```